US00PP37546P2

(12) United States Plant Patent
van Swieten

(10) Patent No.: US PP37,546 P2
(45) Date of Patent: Jul. 28, 2026

(54) ***PHALAENOPSIS* PLANT NAMED 'PHA416323'**

(50) Latin Name: *Phalaenopsis hybrida*
Varietal Denomination: PHA416323

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/316,595

(22) Filed: Sep. 2, 2025

(51) Int. Cl.
*A01H 5/02* (2018.01)
*A01H 5/12* (2018.01)
*A01H 6/62* (2018.01)

(52) U.S. Cl.
USPC ..... Plt./311
CPC ..... *A01H 6/62* (2018.05); *A01H 5/02* (2013.01); *A01H 5/12* (2013.01)

(58) Field of Classification Search
USPC ..... Plt./311
See application file for complete search history.

*Primary Examiner* — Susan Mccormick Ewoldt
(74) *Attorney, Agent, or Firm* — C. Anne Whealy

(57) ABSTRACT

A new and distinct cultivar of *Phalaenopsis* plant named 'PHA416323', characterized by its upright plant habit; moderately vigorous growth habit and moderate growth rate; strong flowering stems; freely flowering habit with typically two inflorescences developing per plant, each inflorescence with numerous flowers; flowers with copper-colored petals and sepals with red-colored venation and purplish red-colored labellum; and good postproduction longevity.

2 Drawing Sheets

Figure 1:
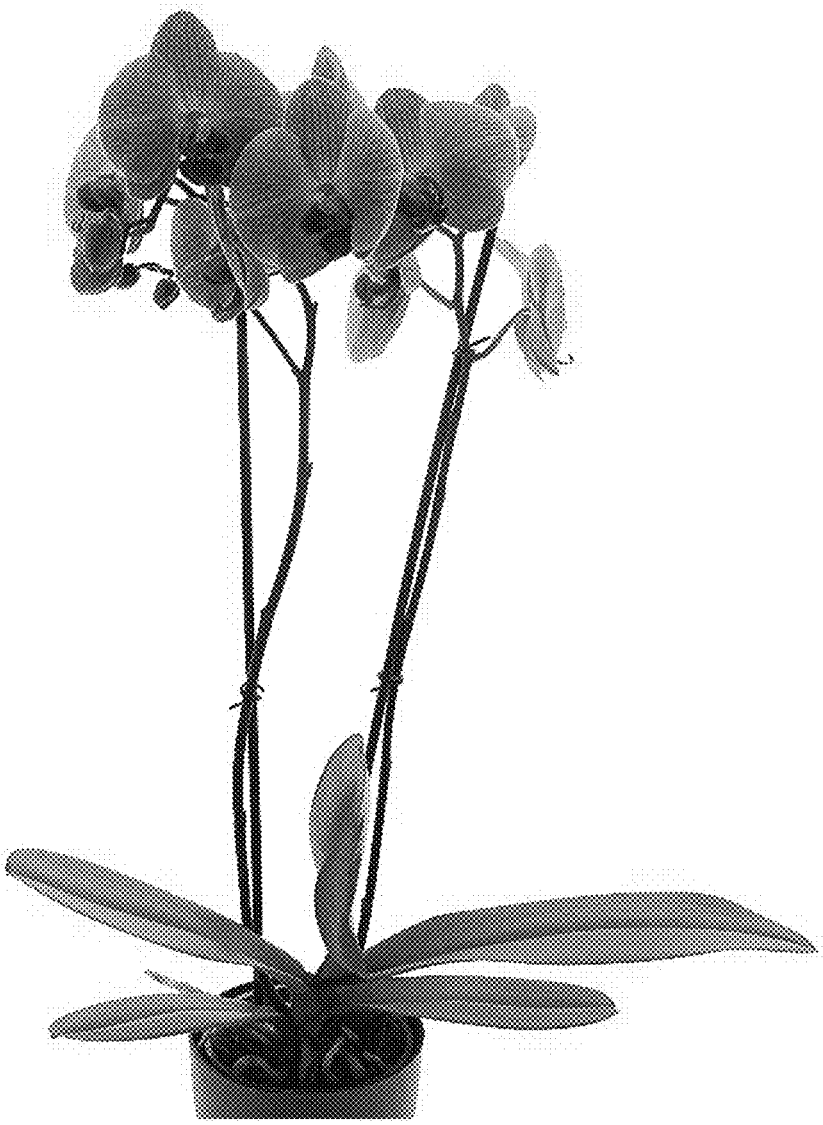

Botanical designation: *Phalaenopsis hybrida.*
Cultivar denomination: 'PHA416323'.

STATEMENT REGARDING PRIOR DISCLOSURES BY INVENTOR and APPLICANT/ASSIGNEE:

A European Community Plant Breeder's Rights application for the instant plant was filed by the Applicant/Assignee of the instant application, Anthura B.V. of Bleiswijk, The Netherlands on Aug. 14, 2024, application number 2024/1891. Foreign priority is not claimed to this application.

BACKGROUND OF THE INVENTION

The present invention relates to a new and distinct cultivar of *Phalaenopsis* plant, botanically known *as Phalaenopsis hybrida,* commonly referred to as a *Phalaenopsis* or Moth Orchid and hereinafter referred to by the name 'PHA416323'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in July 2017 in Bleiswijk, The Netherlands of a proprietary breeding selection of *Phalaenopsis hybrida* identified as code number 14-062051-0001, not patented, as the female, or seed, parent with a proprietary breeding selection of *Phalaenopsis hybrida* identified as code number 08-000001-9246, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in April 2020.

Asexual reproduction of the new *Phalaenopsis* plant by in vitro meristem propagation in a controlled environment in Bleiswijk, The Netherlands since April 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA416323'. These characteristics in combination distinguish 'PHA416323' as a new and distinct *Phalaenopsis* plant:

1. Upright plant habit.
2. Moderately vigorous growth habit and moderate growth rate.
3. Strong flowering stems.
4. Freely flowering habit with typically two inflorescences developing per plant, each inflorescence with numerous flowers.
5. Flowers with copper-colored petals and sepals with red-colored venation and purplish red-colored labellum.
6. Good postproduction longevity.

Plants of the new *Phalaenopsis* can be compared to plants of the female parent selection. Plants of the new *Phalaen-*

*opsis* differ primarily from plants of the female parent selection in the following characteristics:

1. Petals and sepals of plants of the new *Phalaenopsis* have more distinct venation than petals and sepals of plants of the female parent selection.
2. The petal apices of plants of the new *Phalaenopsis* are obtuse and shallow retuse whereas the petal apices of the female parent selection are rounded.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are horizontal whereas leaves of plants of the male parent selection are erect to semi-erect to horizontal.
2. Flowers of plants of the new *Phalaenopsis* are broader than flowers of plants of the male parent selection.

Plants of the new *Phalaenopsis* can be compared to plants of *Phalaenopsis hybrida* 'PHALIFQUDI', disclosed in U.S. Plant Pat. No. 26,831. In side-by-side comparisons, plants of the new *Phalaenopsis* differ primarily from plants of 'PHALIFQUDI' in petal and sepal color as petals and sepals of plants of the new *Phalaenopsis* are copper in color with distinct purplish red-colored venation whereas petals and sepals of plants of 'PHALIFQUDI' are copper in color with faint venation.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA416323' grown in a container.

Figure 2:
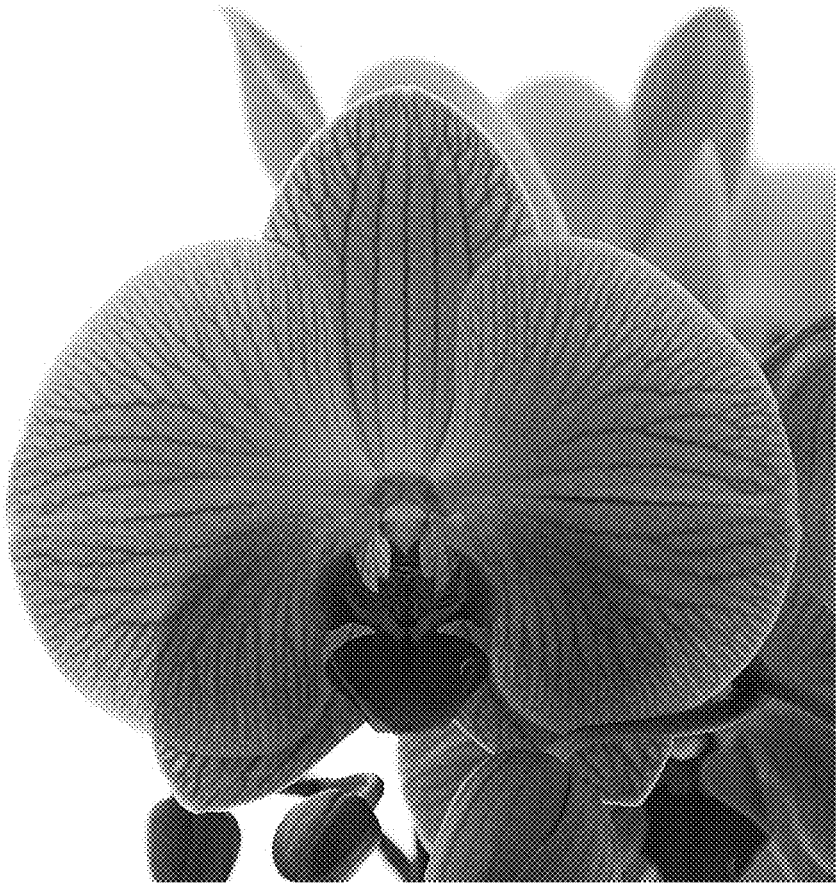

The photograph on the second sheet (FIG. 2) is a close-up view of a typical flower and flower buds of 'PHA416323'.

DETAILED BOTANICAL DESCRIPTION

The aforementioned photographs and following observations and measurements describe plants grown during the winter in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100μmol to 180μmol. In the following description, color references are made to The Royal Horticultural Society Colour Chart, 2015 Edition, except where general terms of ordinary dictionary significance are used.

Botanical classification: *Phalaenopsis hybrida* 'PHA416323'.

Parentage:

*Female, or seed, parent*.—Proprietary breeding selection of *Phalaenopsis hybrida* identified as code number 14-062051-0001, not patented.

*Male, or pollen, parent*.—Proprietary breeding selection of *Phalaenopsis hybrida* identified as code number 08-000001-9246, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane*.—About 20.5 cm.

*Plant height, substrate level to top of floral plane*.—About 53.2 cm.

*Plant diameter or spread*.—About 33.8 cm.

Leaf description:

*Arrangement and quantity*.—Distichous, simple; sessile; about four to six fully-developed leaves per plant.

*Length*.—About 22.8 cm.

*Width*.—About 7.1 cm.

*Aspect*.—Horizontal.

*Shape*.—Oblanceolate; slightly carinate.

*Apex*.—Broadly unequal acute to broadly unequal obtuse.

*Base*.—Sheathing. Sheath length: About 2.4 cm. Sheath width: About 1.3 cm. Sheath color: Close to a blend of 143C and 144B with marginal edges, close to a blend of 137A and 137B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to NN137B; narrow marginal edges, close to 183A. Developing leaves, lower surface: Close to 146A and 146B; margins, close to a blend of N186B and N186C. Fully expanded leaves, upper surface: Close to 146A to 146B; narrow marginal edges, close to 178A; venation, close to NN137B. Fully expanded leaves, lower surface: Close to 144A; margins, close to blend of N186C and 200B; venation, close to NN137C, distally, strongly tinged with close to a blend of N186C and 200B.

Inflorescence description:

*Appearance and flowering habit*.—Showy zygomorphic flowers arranged on axillary simple or branched racemes; typically two inflorescences develop per plant; each inflorescence with about eight flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about eleven weeks on the plant; flowers not persistent.

*Inflorescence length* (*lowermost flower to inflorescence apex*).—About 22.8 cm.

*Inflorescence width*.—About 14.6 cm.

*Flower buds*.—Height: About 1.9 cm. Diameter: About 1.3 cm by 1.7 cm. Shape: Broadly ovate. Color: Close to 174A; distally, close to 178A and 178B; venation, close to 178A.

*Flower size*.—About 8.8 cm (vertical) by 9.7 cm (horizontal).

*Flower depth*.—About 3 cm.

*Petals, quantity and arrangement*.—Three, two lateral petals and one center petal transformed into a labellum.

*Lateral petals*.—Length: About 4.6 cm. Width: About 6.3 cm. Shape: Broadly reniform to close to lunate. Apex: Obtuse and shallow retuse. Margin: Entire; not undulate. Texture and luster, upper and lower surfaces: Smooth, glabrous; velvety; matte. Color: When opening, upper surface: Close to N170C; lower half, close to 179B; towards the margins, close to 162B and 162C; narrow marginal edges, close to 160B; midvein, close to 184A and reticulate venation, close to 182A; veins do not extend to the margins. When opening, lower surface: Close to a blend of 161A and 164D; towards the margins, close to 161A; narrow marginal edges, close to 160B; reticulate venation, close to 182A and 182B; veins do not extend to the margins. Fully opened, upper surface: Close to a blend of N170C and 174D; lower half, close to 181D; towards the margins, close to 162C; narrow marginal edges, close to 160B to 160D; midvein, close to 184A and reticulate venation, close to 185C; veins do not extend to the margins; colors do not change with subsequent development. Fully opened, lower surface: Close to a blend of 160D and 161D; towards the margins, close to a blend of 161C and N170D; narrow marginal edges, close to 160B and 160C; midvein, close to 186B; reticulate venation, close to 185C and 185D; veins do not extend to the margins; colors do not change with subsequent development.

*Labella*.—Appearance: Three-parted with two lateral lobes and a central lobe; overall shape, broadly cordate to reniform. Length, lateral lobes: About 2.1 cm. Width, lateral lobes: About 1.5 cm. Length, central lobe: About 2.5 cm. Width, central lobe: About 9 mm to 21 mm. Length, cirrhose tips: About 1.2 cm. Shape, lateral lobes: Obovate. Shape, central lobe: Ovate-rhomboid with an elongated apex. Apex, lateral lobes: Obtuse. Apex, central lobe: Cleft with cirrhose apices facing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 5 mm in length, about 7 mm in width and about 6 mm in height. Color: When opening, upper surface: Lateral lobes: Close to 183C; towards the apex, close to 64C; towards the base, close to 156C and at the base, close to 13B with axial stripes, close to 183C. Central lobe: Close to 185B; towards the apex, close to 60C; at the base, close to 160A with radial stripes, close to 183C; cirrhose apices, close to 60C. Callosities: Close to 5C; towards the apex, close to 14B; densely covered with fine dots, close to 181A and 181B. When opening, lower surface: Lateral lobes: Close to 186C; towards the apex and lower margins, close to 167B and 167C; at the base, close to 156C with axial stripes, close to 181A and 182A. Central lobe: Close to 70B; central blotch, close to NN155B; towards the apex, close to 181A and 181B; at the base, close to 155A and at the column, close to 186C; cirrhose apices, close to 70B. Fully opened, upper surface: Lateral lobes: Close to 183C; towards the apex, close to 64C; towards the base, close to 156C and at the base, close to 13B with axial stripes, close to 183C. Central lobe: Close to 185B; towards the apex, close to 60C, and at the apex, slightly tinged with close to 163B; at the base, close to 160A with radial stripes, close to 183C; cirrhose apices, close to 60C. Callosities: Close to 12B; towards the apex, close to 14A; densely covered with fine dots, close to 180B. Fully opened, lower surface: Lateral lobes: Close to 186C; towards the apex and lower margins, close to 167B and 167C; at the base, close to 156C with axial stripes, close to 181A and 182A. Central lobe: Close to 70B; central blotch, close to NN155B; towards the apex, close to 181A and 181B; at the base, close to 155A and at the column, close to 186C; cirrhose apices, close to 70B.

*Sepals*.—Quantity and arrangement: Three, one upper dorsal sepal and two lower lateral sepals. Length, dorsal sepal: About 5 cm. Width, dorsal sepal: About 3.8 cm. Length, lateral sepals: About 5 cm. Width, lateral sepals: About 3.4 cm. Shape, dorsal sepal: Elliptic. Shape, lateral sepals: Ovate to close to broadly elliptic. Apex, dorsal and lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 173C; towards the base and the apex, close to 162B; narrow marginal edges, close to 162B and 162C; midvein, close to 182A; reticulate venation, close to 182B; veins do not extend to the margins. When opening, lower surface: Close to 174A; center, close to 161A; narrow marginal edges, close to 160B; midvein, close to 182A; reticulate venation, close to 182B and 182C; veins do not extend to the margins. Fully opened, upper surface: Close to 182D tinged with close to 161D; towards the margins, close to 159B and 159C; narrow marginal edges, close to 159C; midvein, close to 184C; reticulate venation, close to 184D; veins do not extend to the margins. Fully opened, lower surface: Close to a blend of 182D and 185D; broad marginal edges, close to 181D; reticulate venation, close to 184B to 184C.

*Color, lateral sepals*.—When opening, upper surface: Close to a blend of 174C, 176C and 176D; towards the base, close to a blend of 160A and 162A; narrow marginal edges, close to 162B and 162C; midvein and reticulate venation, close to 182A; veins do not extend to the margins. When opening, lower surface: Close to 174B; towards the base, close to 160A; narrow marginal edges, close to 160A and 160B; midvein, close to 182A; reticulate venation, close to 182B and 182C; veins do not extend to the margins. Fully opened, upper surface: Close to 185D tinged with close to 161D; towards the base, close to 160A and 160B; narrow marginal edges, close to 159C; midvein, close to 186A; reticulate venation, close to 186B; veins do not extend to the margins. Fully opened, lower surface: Close to N170D; towards the apex, tinged with close to 182C; at the base, strongly tinged with close to 160C; midvein, close to 185B; reticulate venation, close to 184B to 184D.

*Peduncles*.—Length: About 53.1 cm. Diameter: About 5 mm. Strength: Strong. Aspect: Upright to outwardly arching. Texture and luster: Smooth, glabrous; matte. Color: Close to 200A with dense fine dots, close to N148D.

*Pedicels*.—Length: About 4.2 cm. Diameter: About 3 mm. Strength: Moderately strong. Aspect: About 50° from peduncle axis. Texture and luster: Smooth, glabrous; matte. Color: Close to 186B; proximal end, close to a blend of 183C and 186A.

*Reproductive organs*.—Androecium: Column length: About 1 cm. Column width: About 6 mm. Column color: Close to N78C; at the apex, close to NN155D. Pollinia quantity: Two. Pollinia diameter (per two pollinia): About 2 mm. Pollinia color: Close to 23A. Gynoecium: Stigma length: About 4 mm. Stigma width: About 5 mm. Stigma shape: Reniform. Stigma color: Close to 156D. Ovary length: About 1 cm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA416323' as herein illustrated and described.

* * * * *